United States Patent [19]
Klopotek

[11] Patent Number: 5,651,784
[45] Date of Patent: Jul. 29, 1997

[54] ROTATABLE APERTURE APPARATUS AND METHODS FOR SELECTIVE PHOTOABLATION OF SURFACES

[75] Inventor: Peter J. Klopotek, Framingham, Mass.

[73] Assignee: Summit Technology, Inc., Waltham, Mass.

[21] Appl. No.: 365,060

[22] Filed: Dec. 28, 1994

Related U.S. Application Data

[63] Continuation of Ser. No. 72,797, Jun. 4, 1993, abandoned.

[51] Int. Cl.⁶ .................................................... A61N 5/06
[52] U.S. Cl. .................... 606/5; 606/10; 606/17; 606/4; 128/898
[58] Field of Search .................... 606/2–6, 10–12, 606/17, 18; 128/898

[56] References Cited

U.S. PATENT DOCUMENTS

| | | |
|---|---|---|
| 3,262,122 | 7/1966 | Fleisher et al. . |
| 3,447,862 | 6/1969 | Elpern . |
| 3,558,208 | 1/1971 | Hudson . |
| 3,665,483 | 5/1972 | Becker et al. . |
| 4,139,409 | 2/1979 | Macken et al. . |
| 4,227,210 | 10/1980 | Nixon . |
| 4,388,517 | 6/1983 | Schulte et al. . |
| 4,414,059 | 11/1983 | Blum et al. . |
| 4,461,294 | 7/1984 | Baron . |
| 4,648,400 | 3/1987 | Schneider et al. . |
| 4,686,979 | 8/1987 | Gruen et al. . |
| 4,732,148 | 3/1988 | L'Esperance, Jr. . |
| 4,856,513 | 8/1989 | Muller . |
| 4,887,592 | 12/1989 | Loertscher ........................ 606/5 |
| 4,941,093 | 7/1990 | Marshall et al. . |

(List continued on next page.)

FOREIGN PATENT DOCUMENTS

| | | |
|---|---|---|
| 10224322 | 6/1987 | European Pat. Off. . |
| 0274205A2 | 7/1988 | European Pat. Off. . |
| 0280414A1 | 8/1988 | European Pat. Off. . |
| 296982A | 6/1987 | France . |
| 2246270 | 3/1973 | Germany . |
| 3535073 | 4/1987 | Germany ........................ 606/5 |
| WO91/04829 | 4/1991 | WIPO . |
| 9111158 | 8/1991 | WIPO ........................ 606/5 |
| WO92/00711 | 1/1992 | WIPO . |

OTHER PUBLICATIONS

L. Missotten et al, "Experimental Excimer Laser Keratomileusis", pp. 103–117, 1987.

W.W. Simmons, et al., "Optical Beam Shaping Devices Using Polarization Effects", Applied Optics, vol. 13, No. 7, Jul. 1974, pp. 1629–1632.

Puliafito et al., "Excimer Laser Ablation of the Cornea and Lens, Experimental Studies", Ophthalmology, vol. 92, No. 6, Jun. 1985, pp. 741–748.

Stephen L. Trokel, M.D. et al., "Excimer Laser Surgery of the Cornea", American Journal of Ophthalmology, 1983, 96:710–71.

J.P. Coullahan et al., "Chip Passivation Technique", IBM Technical Disclosure Bulletin, vol. 22, No. 6, Nov. 1979, pp. 2279, 2280, 2281, 285, 2531.

D.J. O'Hara et al., "Holographic Selective Heating System", IBM Technical Disclosure Bulletin, vol. 11, No. 9, Feb. 1969, pp. 1168–1169.

Primary Examiner—Lee S. Cohen
Assistant Examiner—Michael Peffley
Attorney, Agent, or Firm—Thomas J. Engellenner; Carolyn d'Agincourt; Lahive & Cockfield

[57] ABSTRACT

Apparatus and methods to modify the intensity distribution of a beam of radiation, such as a laser, and for eroding surfaces with predetermined shapes. A rotatable mask is formed with one or more apertures that have a geometric spiral shape originating substantially the center of rotation on the mask. The mask is insert to the beam for modification of the intensity of that beam, and additionally to form the desired etch pattern on a target surface. In a preferred embodiment, the invention is useful for performing kerotoplasty or keratomileusis.

17 Claims, 5 Drawing Sheets

U.S. PATENT DOCUMENTS

| | | |
|---|---|---|
| 4,953,969 | 9/1990 | Fedorov . |
| 4,973,330 | 11/1990 | Azema et al. . |
| 4,994,058 | 2/1991 | Raven et al. . |
| 5,019,074 | 5/1991 | Muller . |
| 5,109,465 | 4/1992 | Klopotek . |
| 5,147,352 | 9/1992 | Azema et al. . |
| 5,411,501 | 5/1995 | Klopotek ................................. 606/4 |

5,651,784

ROTATABLE APERTURE APPARATUS AND METHODS FOR SELECTIVE PHOTOABLATION OF SURFACES

This application is a continuation of application Ser. No. 08/072,797, filed on Jun. 4, 1993, (now abandoned).

BACKGROUND OF THE INVENTION

This invention relates generally to methods and apparatus for modifying the spatial exposure distribution of a laser beam. It relates also to methods and apparatus for ablating surfaces through use of a photoablative laser. Most particularly, the invention relates to methods and reprofiling for eroding the surface of the cornea through laser keratoplasty or keratomileusis to correct certain of the vision deficiencies, such as myopia.

Lasers are commonplace today. They have wide-ranging utility in most of the applied sciences and engineering. Often, laser systems are developed to generate a laser beam with uniform cross-sectional exposure, such that any portion of the beam has approximately equal energy density. This is achieved, for example, by coupling the beam to complex optical systems, or by selecting only a small portion of the Gaussian intensity distribution, that characterizes most lasers, to approximate uniform intensity.

Alternatively, in certain uses of laser energy, it can be advantageous to employ a laser beam of predetermined and non-uniform cross-sectional intensity. Thus it is one object of this invention to provide apparatus and methods for modifying the spatial intensity distribution of a laser beam to a predetermined distribution.

In particular, lasers can be used to ablate surfaces in a controlled manner. Such ablation depends upon the interaction between the surface structure and the laser radiation, which has a known wavelength and energy density. In addition, the ablation of a surface by laser radiation is typically time-rate dependent, although this time dependency may be non-linear with ablative depth.

Improved ablative precision is often obtained through the use of pulsed laser radiation. Short pulses provide controlled depth etching in the application area. This control is especially important in photorefractive keratectomy, a type of keratomileusis procedure, where the anterior surface of the cornea is ablated to correct certain visual deficiencies such as near-sightedness. By careful application of laser radiation to the cornea, the refractive power of the eye can be changed with precision.

By successive application of laser pulses to a surface, and by altering the size of the exposure area, curvatures can be created or removed on a surface. For example, when the ablative technique begins by irradiation of a large circular area, and progressively decreases the radius of the exposed area while maintaining approximately the same energy density, the central region will have the greatest ablative depth because it is exposed to a larger amount of cumulative, ablative radiation over the duration of the procedure. Conversely, the outermost regions have the least ablative depth. If the surface were initially flat, the resulting profile would be concave. If the surface is initially convex, the surface curvature can be flattened. In photorefractive keratectomy, the curvature on the cornea, i.e. the difference between the cornea's ideal curvature and the patient's actual corneal shape, is corrected.

It is an object of this invention to provide improved apparatus and methods for performing laser kerotoplasty and keratomileusis. In the prior art, for example in U.S. Pat. No. 4,665,913, by L'Esperance entitled "Method for Ophthalmological Surgery", are disclosed for reprofiling the cornea through the use of a laser scalpel or by laser scanning techniques that are especially difficult to control. The L'Esperance '913 patent requires precise control of a laser spot on the cornea, and further requires that the complex etching pattern be carefully followed. Such scanning techniques leave much room for error and thus require expensive safeguards for surgical applications. Additionally, these methods are naturally time-consuming since only a small portion of the surface is ablated at a given time.

Accordingly, it is an object of this invention to apply laser energy to a corneal surface with improved control of using a laser that does not require scanning action.

Another technique for corneal reshaping using an laser photoablation apparatus comprises controlling the reprofiling operation by varying the size of the surface area to which the pulses of laser energy are applied. In one embodiment, a beam-shaping stop or window is moved axially along the beam to increase or decrease the area of the light incident on cornea. Alternatively, an adjustable iris can be disposed in the beam path. In either approach, by progressively altering the size of the exposed region, the desired photoablation profile is established on the corneal surface. For further details on this technique, see Marshall et al, "Photo-Ablative Reprofiling of the Cornea Using an Excimer Laser: Photorefractive Keratectomy," 1 Lasers in Ophthalmology, 21–48 (1986), and U.S. Pat. No. 4,941,093, incorporated herein by reference.

Yet another technique for corneal reshaping involves the use of a laser photoablation apparatus in which a beam-shaping mask is disposed between the laser and the surface. The mask provides a predefined profile of resistance to laser radiation erosion by selectively absorbing some of the laser radiation while permitting the remainder to be transmitted to the surface in accordance with the mask profile. For further details of such erodible masking techniques, see U.S. Pat. No. 4,856,513, 4,994,058 and 5,019,074 incorporated herein by reference.

It is another object of this invention to provide further apparatus and methods for ablating a surface, such as a cornea, by applying laser energy to the surface with selectable exposure distributions.

These and other objects of the invention are evident in the description that follows.

SUMMARY OF THE INVENTION

Apparatus and methods are disclosed for modifying the spatial intensity distribution of a beam of radiation. In one aspect, a mask having at least one transmissive aperture is rotated about a rotation point that is co-aligned to the beam, preferably at its center. The aperture originates substantially at the rotation point and forms a geometric spiral shape which expands outwardly. The aperture further has a transmissive width which changes progressively along the length of the spiral shape. As the mask is rotated about the rotation point, a beam of radiation incident on the mask is transmitted therethrough with the intensity that varies in accordance with the design or properties of the mask and as a function of radial position with respect to the rotation point.

According to other aspects of the invention, the rotational direction of the geometric spiral shape formed by each aperture is clockwise, relative to and around the rotation point; alternatively it is counter-clockwise.

According to other aspects of the invention, the width of the aperture increases functionally as the distance to the rotation point increases; alternatively, the width decreases as the distance to the rotation point increases.

In yet another aspect, the aperture can comprise a plurality of apertures, preferably oriented such that each of the apertures expands outwardly and in the same rotational direction, e.g., clockwise or counter-clockwise, as every other aperture. The plurality of apertures are also preferably oriented to be equally spaced relative to one another.

In another aspect, the invention provides a system for modifying the spatial intensity distribution of a beam of radiation. The system includes a mask, such as described above, and a rotation means for rotating the mask. A beam of radiation incident to the mask is thus modified according to the characteristics of the mask.

The invention also provides for a system to erode a surface into various shapes. A laser is employed which generates a beam of laser light at a wavelength and power sufficient to ablate the target surface. A mask, such as described above, is aligned to the beam such that the laser is incident on the mask. When the mask is rotated, the beam is transmitted through the mask with a modified exposure profile that accordingly ablates the target surface as a function of that profile, which is substantially symmetric about the rotation point.

In other aspects, the system for eroding a surface can include imaging optics to image the rotating mask onto the target surface. The system can further include orientation means for tilting the mask relative to the optical axis to thereby form a surface astigmatically, instead of symmetrically.

A further aspect of the invention provides a method for modifying the spatial intensity distribution of a beam of radiation. The method includes the steps of inserting a mask, such as described above, into the beam and rotating the mask to modify the intensity characteristics of the beam according to the transmission characteristics of the mask.

The method is enhanced further, according to another aspect, to erode a target surface according to the modified intensity of a beam of radiation when the beam illuminates a surface, such as a cornea. When a need exists to erode the surface astigmatically, the invention further provides for the additional step of tilting the mask means relative to the optical axis to ablate the surface astigmatically.

In other aspects, the method includes the step of imaging the mask onto the target surface, such as the cornea. For example, in corneal surgery, the intensity distribution of the beam as modified by the mask is imaged directly onto the cornea to fit the patient's eye. Thus, a user can select a predetermined exposure distribution to effect a desired correction on the corneal surface.

The invention will next be described in connection with certain preferred embodiments; however, it should be clear that various additions, subtractions, and modifications can be made by those skilled in the art without departing from the scope of the invention.

BRIEF DESCRIPTION OF THE DRAWINGS

A more complete understanding of the invention may be obtained by reference to the drawings in which.

DETAILED DESCRIPTION OF ILLUSTRATED EMBODIMENTS

Figure 1:
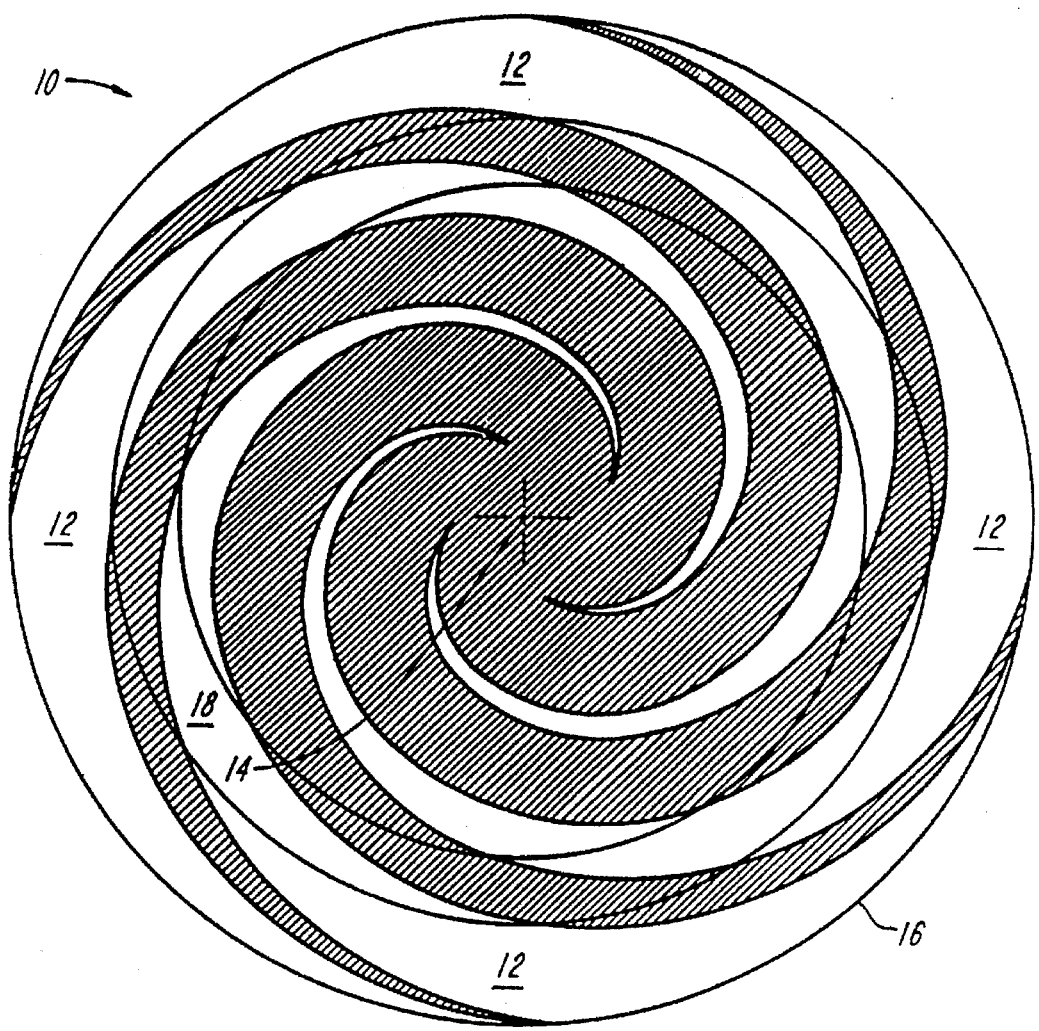
FIG. 1 illustrates a mask constructed in accordance with the invention.

FIG. 1 illustrates a mask 10 constructed in accordance with the invention having four transmissive apertures 12 oriented respective to the center 14 of the mask 10. Each of the apertures 12 has a geometric spiral shape that originates substantially from the mask's center 14 and expands outwardly while rotating counter-clockwise about the center 14. The functional width of each of the apertures 12 progressively increases along the length of the spiral shape, starting near the center 14 and continuing to the edge 16.

It can thus be seen from FIG. 1 that relatively more total aperture exists towards the edge 16, which is largely transmissive, as compared to the center 14, which is largely opaque. This is effectively illustrated by the incremental annulus 18 overlaid on the mask 10. The integrated area of all the transmissive apertures over-lapped by the annulus 18 changes as the radius of the annulus changes. In its illustrated position, for example, the integrated area of all of the transmissive apertures 12 that lie within the annulus 18 would be smaller than if the annulus 18 were situated closer to the center, i.e., with a smaller internal radius. Likewise, if the annulus 18 were positioned nearer to the edge 16, i.e., such that the annulus had a larger internal radius, the integrated area of all of the transmissive apertures 12 that lie within the annulus 18 would be greater than that of its illustrated position.

In operation, the mask 10 is rotated about its center 14. When a beam of radiation is incident on the mask 10, preferably aligned such that its optical axis joins with the center 14 and such that its beam substantially fills the mask 10, it is transmitted therethrough with varying exposure relative to the radial distance from the center 14.

Figure 2:
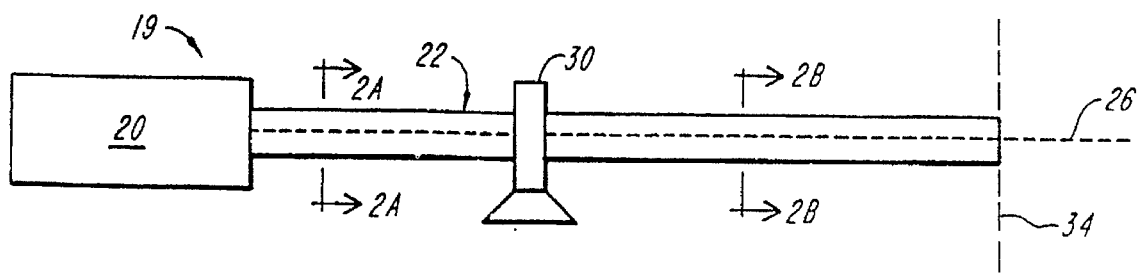
FIG. 2 is a schematic illustration of apparatus for practicing a method of modifying the spatial exposure distribution of a beam of radiation in accordance with the invention.
Figure 2A:
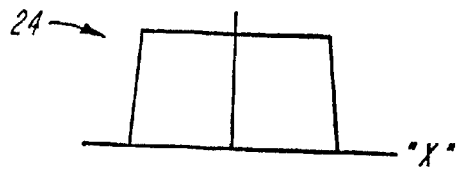
FIG. 2A is a graph of the intensity profile of a beam of laser radiation before passage through the mask of FIG. 2.
Figure 2B:
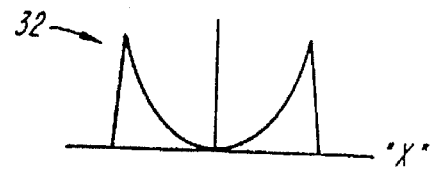
FIG. 2B is a graph of the exposure profile of a beam of laser radiation after passage through the mask of FIG. 2.

FIG. 2 illustrates how a mask 10 is utilized by showing a schematic layout of a system 19 for modifying the intensity profile of a laser beam to a predetermined cross-sectional exposure distribution. A laser 20 generates a beam 22 that has a relatively uniform cross-sectional intensity distribution, as illustrated in the graph 24 of FIG. 2A which shows the spatial intensity distribution of a cross-sectional slice of the beam (denoted as dimension "x"). The beam 22 is incident on the mask apparatus 30, which is similar to the mask 10 shown in FIG. 1 except that it is held by a supporting structure which rotates the mask about its center, co-aligned to the axis 26. After transmitting through the mask apparatus 30, the beam 22 has a cumulative exposure profile, as illustrated by the graph 32 of FIG. 2B which shows a cross-sectional slice of the cumulative exposure 22 after passing through the rotatable mask apparatus 30.

Provided the beam 22 is of the type which has ablative strength relative to the target surface, the modified beam 22 can etch a surface 34 with a shape similar to that of its cross-sectional exposure, for example, the profile illustrated in the graph 32.

The methods and materials for manufacturing the mask 10 of FIG. 1 are numerous. Generally, a blocking material suitable for inhibiting the transmission of radiation at the wavelength of interest can create the apertures 12 when coated on a blank substrate which transmits the radiation. For example, glass represents a common and useful transmissive material for the visible light spectrum, and glass is easily coated with light-blocking black paint to create the apertures 12. Likewise, in the ultra-violet spectrum, e.g., as generated by an excimer laser, surface metalizations or standard UV-blocking coatings can be used to block the radiation to thereafter create the apertures 12.

The procedures for constructing the apertures 12 depend upon the methods used to create the mask 10. Photolithographic techniques, laser scribing, or other modern etch or masking techniques can be used to create the mask 10. In some applications, it may be preferable to etch or machine a physical hole in the structure forming the mask 10 to thereby create the apertures 12. Well-known techniques and systems exist for making accurate measurement targets, for example "four-bar targets" in modulation transfer function (MTF) testing, and the same techniques and systems can form a mask 10 accurately. Accordingly, apertures 12 could be formed by machining and tooling or, if higher accuracy is required, by laser etching.

If the mask 10 is used in combination with a relatively high energy laser, the method of manufacturing the mask 10 may be limited to materials and techniques which can withstand the laser energy without damage. Fortunately, however, a laser beam is preferably transmitted through the mask 10 in an expanded or collimated beam, rather than at a focus. This tends to mitigate the potential damage which can be caused by the laser. Alternatively, the mask can be designed for "one-off" or disposable wedge.

If the mask 10 is re-usable, it can be stored in a catalog for later use, along with a series of other masks to provide a user with a broad selection of exposure distributions via a single laser beam.

The mask 10 illustrated in FIG. 1 is illustrative rather than limiting. For example, those skilled in the art will understand that such a mask can also be formed by apertures 12 which are oriented clockwise about the center 14. Furthermore, those skilled in the art should recognize that the apertures 12 can instead contain a light-blocking material; and that the illustrated black regions between the apertures 12 can instead be light-transmitting apertures. In such a configuration, the functional width of each of the apertures would progressively decrease along with the length of the spiral shape starting near the center 14 and continuing to the edge 16. Such an embodiment, when used for photorefractive keratectomy, can be used to correct myopia by reducing the corneal curvature.

Alternatively, the apertures 12 can be formed with reflective material, like mirrored elements, whereby the mask 10 is utilized in reflection as opposed to transmission.

It is equally apparent to those skilled in the art that the number of apertures 12 are also illustrative, as are the radial orientation of the spiral shape of each. For example, apertures 12 are easily constructed with several more apertures 12 and in a clock-wise orientation, if desired, all in accordance with the teachings of the invention.

Figure 3:
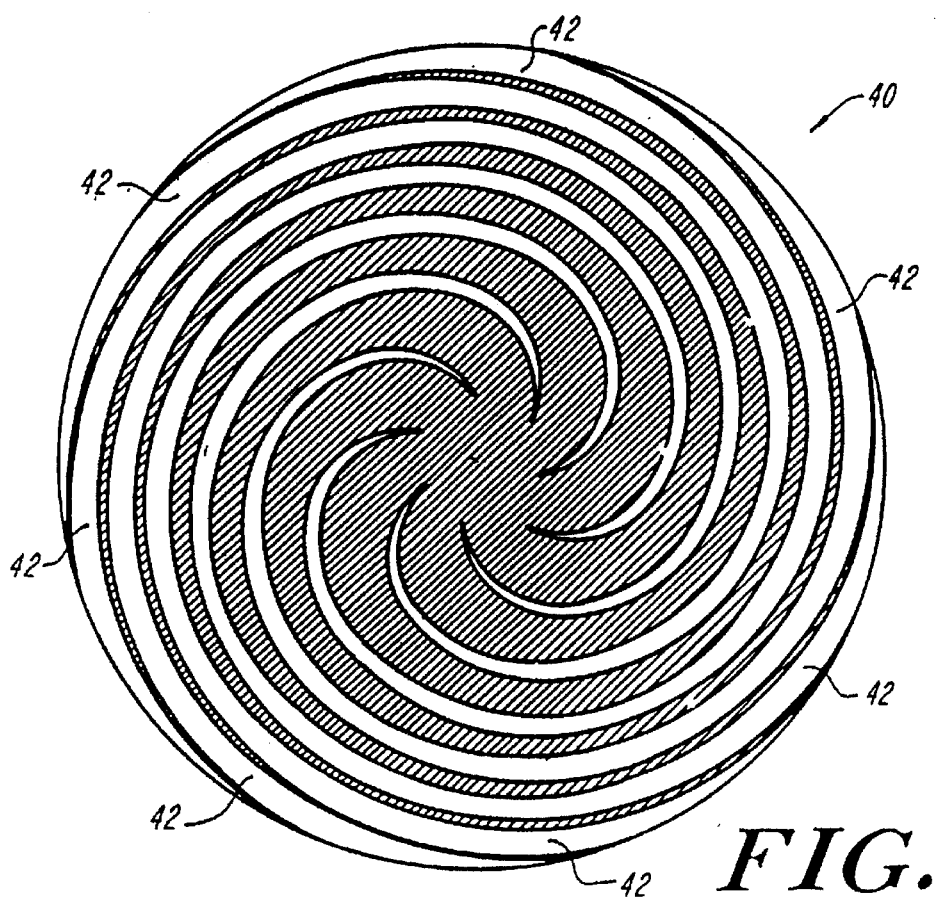
FIG. 3 illustrates another embodiment of a mask constructed in accordance with the invention.
Figure 4:
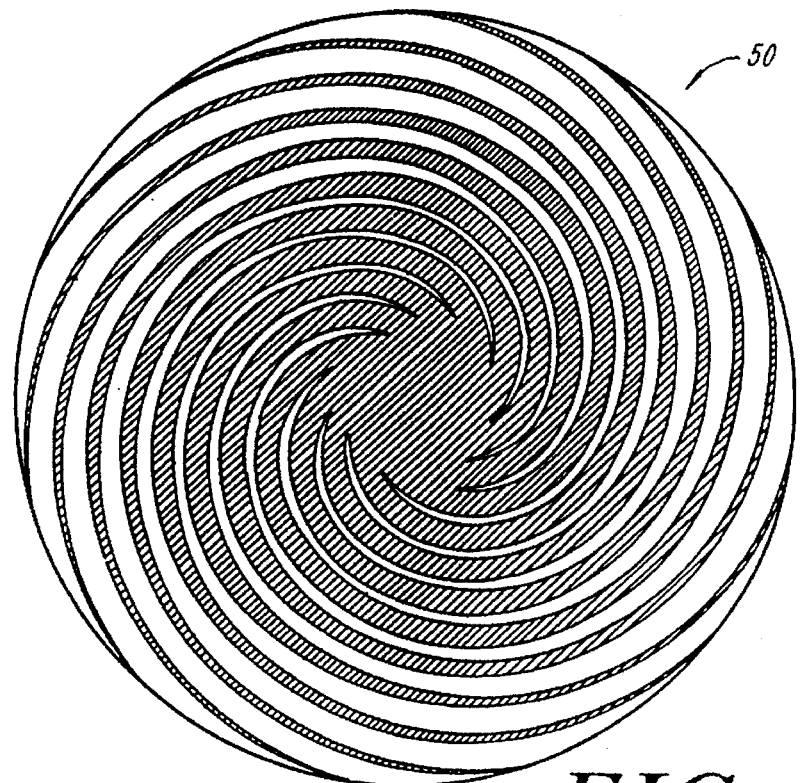
FIG. 4 illustrates another embodiment of a mask constructed in accordance with the invention.
Figure 5:
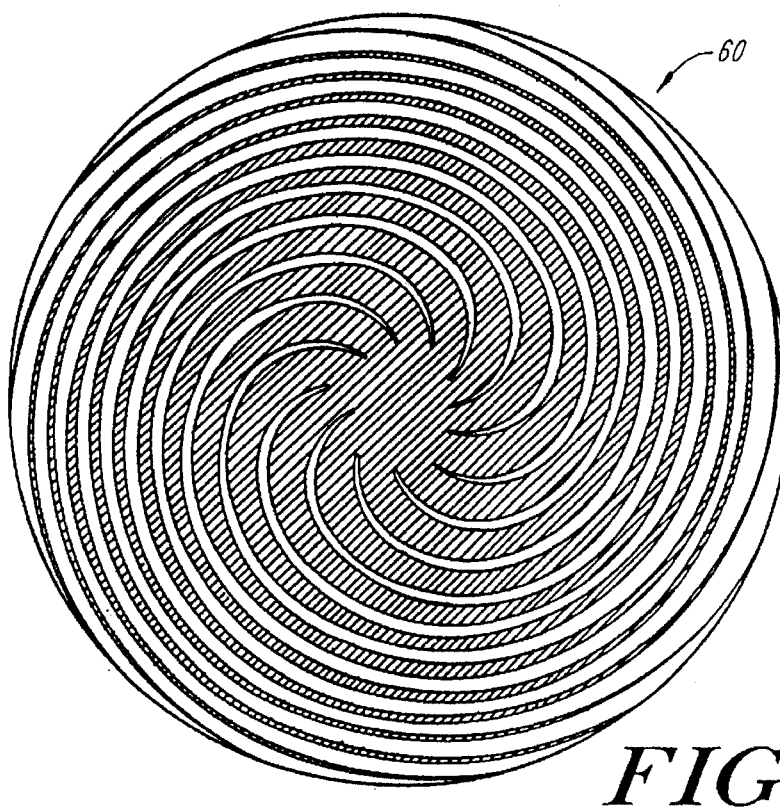
FIG. 5 illustrates another embodiment of a mask constructed in accordance with the invention.

FIGS. 3, 4, and 5 illustrate other masks constructed in accordance to the invention, and for use in each system or apparatus described herein. FIG. 3 illustrates a mask 40 having seven spiral apertures 42 originating substantially near to the center of the mask 40 and expanding outwardly in a counter-clockwise direction.

FIGS. 4 and 5 illustrate similarly constructed masks, each having eleven apertures, and each providing similar cumulative exposures. They differ in the details of the design of the spiral apertures. In the mask 40, the angular speed of the spiral apertures are a growing function of the distance from the center; while in the mask 50, the angular speed of the spiral apertures are not a function of the distance from the center.

The masks portrayed in FIGS. 1, 3–5 have an advantage over prior designs in that they are more insensitive to motion relative to the optical axis. The spiral shaped apertures are thus less prone to etching surface errors on the target surface due to system misalignments or target movement.

It should also be clear that the spiral-shaped patterns can be multivariant, particularly to create regions where a different curvature is desired. For example, the tapered edges of the masks shown in FIGS. 1, 3–5 can be flaired to create blend zones at the periphery of the reprofiled cornea.

Figure 6:
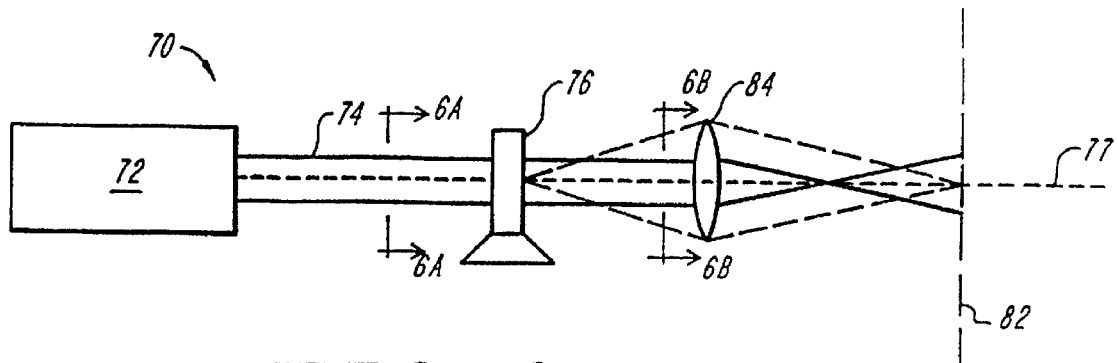
FIG. 6 is a schematic illustration of apparatus for practicing a method of eroding a target surface in accordance with the invention.
Figure 6A:
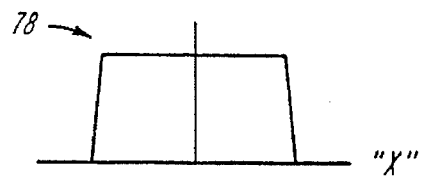
FIG. 6A is a graph of the initial intensity profile of a beam of laser radiation before passage through the mask of FIG. 6.
Figure 6B:
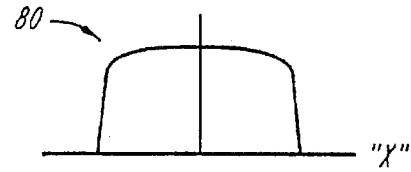
FIG. 6B is a graph of the cumulative exposure profile of a beam of laser radiation after passage through the mask of FIG. 6.

FIG. 6 illustrates schematically a system 70 constructed in accordance with the invention for eroding a surface, such as a cornea. Similar to the system 19 shown in FIG. 2, the system 70 includes a laser 72 to generate a laser beam 74 which is co-aligned with the mask apparatus 76 along an optical axis 77. The beam 74 exhibits substantially uniform cross-sectional intensity prior to modification by the mask apparatus 70, as illustrated by the graph 78 in FIG. 6A. Once the beam is transmitted through the mask apparatus 76, the beam has a modified exposure distribution, as illustrated by the graph 80 in FIG. 6B, dependent upon the characteristics of the mask.

The cumulative exposure profile illustrated in the graph 80 is thus typical to erode the surface 82 into a similar shape. Preferably, one or more optical components 84 image the mask 76 onto the surface 82 in a controlled magnification to achieve the desired shape and size of the eroded surface. For example, in corneal surgery, the magnification would preferably image the mask 76 directly onto and within the dimensions of the patient's cornea to achieve the desired curvature. If the cumulative exposure profile were similar to the distribution shown in graph 80, for example, the patient's cornea is ablated in greater amounts in the center, i.e. nearer the optical axis, and less towards the edges of the beam. This type of illumination is typical for patients suffering from myopia, where the cornea has too much optical power and the proper correction is to flatten the cornea to an ideal curvature.

Figure 7:
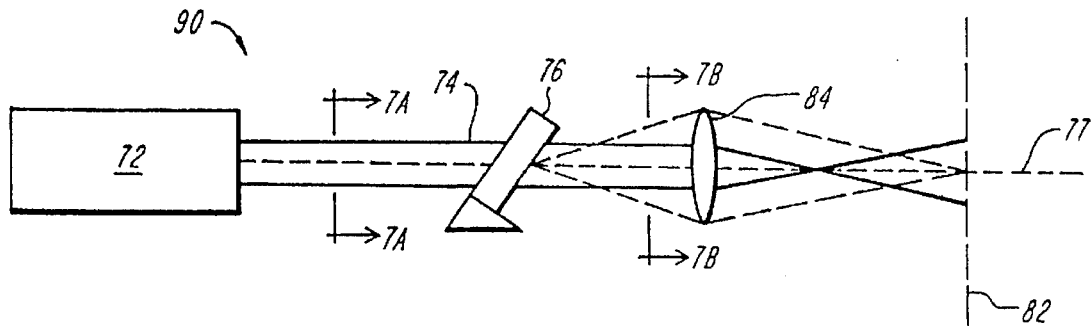
FIG. 7 is a schematic illustration of apparatus for practicing a method of eroding a surface astigmatically in accordance with the invention.
Figure 7A:
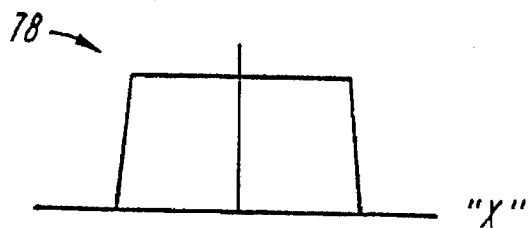
FIG. 7A is a graph of the initial intensity profile of a beam of laser radiation before passage through the mask of FIG. 7.

FIG. 7 illustrates yet another feature of the invention whereby a system constructed in accordance with the invention erodes a surface astigmatically. The system 90 is identical to system 70 of FIG. 6 except that the mask apparatus 76 is tilted along the optical axis 77. Accordingly, the modified exposure distribution of the laser beam 74 after the mask apparatus 76 is bi-axial and differs along the respective axes. Graph 78 in FIG. 7A illustrates the initial intensity profile of beam 74 before processing.

Figure 7B:
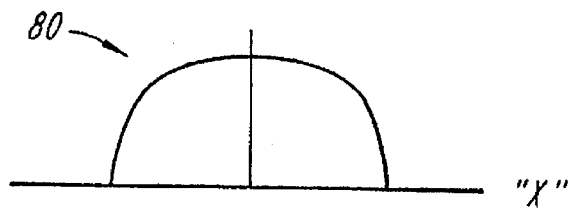
FIG. 7B is a graph of the exposure profile of a beam of laser radiation along one transverse axis after passage through the mask of FIG. 7.
Figure 7C:
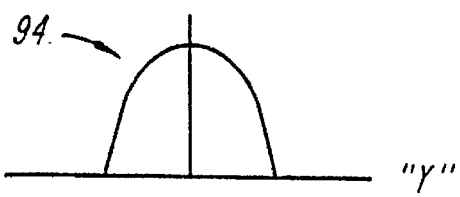
FIG. 7C is a graph of the cumulative exposure profile of a beam of laser radiation along an orthogonal axis relative to that shown in FIG. 7B, after passage through the mask of FIG. 7.

Graph 80 in FIG. 7B illustrates the exposure distribution along the "x" axis, which in the drawings represents the axis perpendicular to the page. Graph 94 in FIG. 7C on the other hand illustrates the exposure distribution of the beam 74 in the plane of the paper. This distribution is more pronounced than its counter-part in graph 80 and thus effects a stronger change in the refractive power of the surface. The net effect of the bi-axial distributions shown in graphs 80 and 94 is to erode the surface 82 astigmatically. Such an erosion is often required for patients having astigmatisms; and the astigmatic correction is possible through the system 90 illustrated in FIG. 7.

What has been described thus far is a description of several illustrated embodiments of the invention. It should be understood that modifications are easily made to these illustrations without departing from the full scope of the invention. For example, it should be apparent to those skilled in the art that the invention as described herein is easily adaptable to lasers which do not exhibit substantially uniform spatial intensity prior to modification. Often, in fact, lasers do not have uniform cross-sectional intensities. Nevertheless, provided the mask apertures and spiral shapes are designed appropriately to accommodate the non-uniform laser beam, the invention can still provide a predetermined spatial exposure distribution after modification by the mask.

What I claim is:

1. Apparatus for modifying the spatial intensity distribution of a beam of radiation, comprising a mask for producing a predetermined transmitted spatial exposure distribution from an incident spatial intensity distribution, said mask being rotatable about a rotation point and having at least one transmissive aperture oriented respective to said rotation point, said aperture having a geometric spiral shape that originates substantially from said rotation point and expands outwardly and further having a transmissive width that changes progressively along the length of said spiral shape, such that said transmitted spatial exposure varies as a function of radial position with respect to said rotation point; and an orientation device for tilting said mask relative to an optical axis to erode a surface astigmatically.

2. Apparatus of claim 1 wherein said rotational direction of the spiral shaped aperture is clockwise.

3. Apparatus of claim 1 wherein said rotational direction of the spiral shaped aperture is counter-clockwise.

4. Apparatus of claim 1 wherein said width increases as the distance to said rotation point increases.

5. Apparatus of claim 1 wherein said width decreases as the distance to said rotation point increases.

6. Apparatus of claim 1 wherein said aperture comprises a plurality of apertures, each of said apertures expanding outwardly in the same rotational direction as every other of said apertures.

7. A system for modifying the spatial intensity distribution of a beam of radiation, comprising:

(i) a mask optically aligned to said beam of radiation and being rotatable about a rotation point, said mask forming a plurality of transmissive apertures oriented respective to said rotation point wherein each of said apertures has a geometrical spiral shape that originates substantially from said rotation point and expands outwardly in the same rotational direction as every other of said apertures, each of said apertures further having a transmissive width that changes progressively along the length of said spiral shape, (ii) a rotation device for rotating said mask about said rotation point such that a beam of radiation incident on said mask is transmitted therethrough with a modified spatial exposure profile that is substantially symmetric about said rotation point, and (iii) an orientation device for tilting said mask relative to an optical axis to erode a surface astigmatically.

8. A laser system for eroding a surface, comprising:

(i) a laser for generating a beam of laser light that can produce photoablation along an optical axis, (ii) a mask optically aligned to and being rotatable about said optical axis, for modifying the spatial intensity distribution of said beam incident thereon, said mask having at least one transmissive aperture oriented respective to said optical axis, and having a geometric spiral shape that originates substantially from said optical axis and expands outwardly, and further having a transmissive width that changes progressively along the length of said spiral shape, (iii) a rotation device for rotating said mask about said rotation point such that a beam of radiation incident on said mask is transmitted therethrough with a modified spatial exposure profile that is substantially symmetric about said rotation point, and (iv) an orientation device for tilting said mask relative to said optical axis to erode said surface astigmatically.

9. A laser system according to claim 8 further wherein said aperture comprises a plurality of apertures, each of said apertures expanding outwardly in the same rotational direction as every other of said apertures.

10. A laser system according to claim 8 further comprising an imaging device aligned to said optical axis and arranged to image said mask onto said surface whereby radiation passing through said rotation device will impinge upon and erode said surface in accordance with said modified exposure pattern.

11. Apparatus for modifying the spatial intensity distribution of a beam of radiation, comprising a mask for producing a predetermined reflected spatial exposure distribution from an incident spatial intensity distribution, said mask being rotatable about a rotation point and having at least one reflector element oriented respective to said rotation point, said reflector element having a geometric spiral shape that originates substantially from said rotation point and expands outwardly, and further having a reflective width that changes progressively along the length of said spiral shape, such that said reflected spatial exposure varies as a function of radial position with respect to said rotation point; and an orientation device for tilting said mask relative to an optical axis to erode a surface astigmatically.

12. Apparatus according to claim 11 wherein said reflector element comprises a plurality of reflector elements, each of said elements expanding outwardly in the same rotational direction as every other of said elements.

13. A method for modifying the spatial intensity distribution of a beam of radiation, comprising the steps of:

(i) inserting a mask into said beam of radiation, said mask being rotatable about a rotation point and having at least one transmissive aperture oriented respective to said rotation point, said aperture having a geometric spiral shape that originates substantially from said rotation point and expands outwardly and further having a transmissive width that changes progressively along the length of said spiral shape, said mask having a predetermined transmission profile extending radially from said rotation point, (ii) rotating said mask about said rotation point, and (iii) tilting said mask relative to an optical axis to erode a surface astigmatically.

14. A method for eroding a surface by a beam of radiation, comprising the steps of:

(i) generating said beam of radiation along an optical axis aligned to said surface, said beam being of the type which induces photoablation of said surface, (ii) aligning a mask to said beam of radiation, said mask being rotatable about a rotation point and having a plurality of transmissive apertures oriented respective to said rotation point, each of said apertures having a geometric spiral shape that originates substantially from said rotation point and expands outwardly in the same rotational direction as every other of said apertures and further having a transmissive width that changes progressively along the length of said spiral shape, said mask having a predetermined transmission profile extending radially from said rotation point, (iii) rotating said mask about said optical axis, and (iv) tilting said mask relative to said optical axis to erode said surface astigmatically.

15. The method according to claim 14, comprising the further step of imaging said mask onto said surface.

16. A method for correcting corneal refractive anomalies, comprising:

(i) generating a laser beam along an optical axis to a corneal surface, said laser beam being of the type which induces photoablation of said corneal surface, (ii) inserting a mask into said laser beam, said mask being rotatable about said optical axis and having at least one transmissive aperture oriented respective to said optical axis, said aperture having a geometric spiral shape that originates substantially from said optical axis and expands outwardly and further having a transmissive width that changes progressively along the length of said spiral shape, (iii) rotating said mask about said optical axis, (iv) transmitting said laser beam incident on said mask therethrough to achieve a modified spatial exposure profile that is substantially symmetric about said optical axis, said modified spatial exposure profile being selectable by adjusting said shape and said width to effect a desired correction on said corneal surface, and (v) tilting said mask relative to said optical axis to erode said corneal surface astigmatically.

17. The method according to claim 16 wherein said mask comprises a plurality of aperture, each of said apertures expanding outwardly in the same rotational direction as every other of said apertures.

* * * * *